United States Patent [19]

Gilson et al.

[11] Patent Number: 5,203,774
[45] Date of Patent: Apr. 20, 1993

[54] DEVICE FOR USE WITH A CATHETER

[75] Inventors: James P. Gilson, County Galway, Ireland; Anthony F. Rickards, London, England

[73] Assignee: C. R. Bard Ireland Limited, Galway, Ireland

[21] Appl. No.: 647,267

[22] Filed: Jan. 29, 1991

[30] Foreign Application Priority Data

Jan. 30, 1990 [IE] Ireland ................. 330/90

[51] Int. Cl.⁵ .................................. A61M 5/178
[52] U.S. Cl. ......................... 604/165; 604/248; 604/168; 604/169; 604/171
[58] Field of Search ............ 604/256, 9, 52, 53, 604/164–170, 171, 280, 283, 905; 128/344, 348.1

[56] References Cited

U.S. PATENT DOCUMENTS

| | | | |
|---|---|---|---|
| 4,149,535 | 4/1979 | Volder | 604/43 |
| 4,525,157 | 6/1985 | Vaillancourt | 604/52 |
| 4,563,176 | 1/1986 | Gustavsson et al. | 604/280 |
| 4,646,742 | 3/1987 | Packard et al. | 600/194 |
| 4,655,746 | 4/1987 | Daniels et al. | 604/101 |
| 4,723,550 | 2/1988 | Bales et al. | 604/256 |
| 4,838,269 | 6/1989 | Robinson et al. | 604/165 |
| 4,842,591 | 6/1989 | Luther | 604/905 |
| 4,929,243 | 5/1990 | Koch et al. | 604/905 |
| 4,935,010 | 6/1990 | Cox et al. | 604/905 |
| 5,062,836 | 11/1991 | Wendell | 604/167 |
| 5,106,054 | 4/1992 | Mollenauer et al. | 604/905 |

FOREIGN PATENT DOCUMENTS 0267584 5/1988 European Pat. Off. .
8906986 8/1989 PCT Int'l Appl. .
1514019 6/1978 United Kingdom .

*Primary Examiner*—C. Fred Rosenbaum
*Assistant Examiner*—Chalin Smith
*Attorney, Agent, or Firm*—Dennison, Meserole, Pollack & Scheiner

[57] ABSTRACT

The device for use with a catheter includes a sleeve 21 for assembly onto the shaft of a catheter 1, between the catheter shaft and a Tuohy-Borst connector 3. The internal diameter of the sleeve 21 is complementary with the external diameter of the catheter 1 so that the catheter is movable within the sleeve. The external diameter of the sleeve is such that when the Tuohy-Borst connector is closed, a seal is formed between the sleeve and the connector. A flange 24 is provided at one end of the device for engagement with the connector, to prevent movement of the sleeve with the catheter. The internal diameter of the sleeve 21 is also complementary with the external diameter of the catheter 1 so as to provide an annular space about the catheter whereby, in use, a controlled amount of backbleed of blood is allowed.

6 Claims, 2 Drawing Sheets

DEVICE FOR USE WITH A CATHETER

The present invention relates to a device for use with a catheter by medical personnel.

Catheters may be introduced into the human body as part of diagnostic or treatment procedures. They are introduced into organs, for example the heart, via blood vessels which lead into the organ. In standard use, the technique for advancing a catheter and wire requires the opening of a Tuohy-Borst connector mounted on the catheter, moving the catheter to its required site within the body and reclosing the connector.

The standard practice presents a number of difficulties. Firstly, overtightening of the Tuohy-Borst connector on reclosure can impair catheter movement and manipulation. Secondly, small diameter catheters make positive, sealing, closure of the Tuohy-Borst connector difficult. Thirdly, during manipulation of the catheter while the Tuohy-Borst connector is open, severe backbleed occurs from the blood vessels. The backbleed may continue for an extended period while the catheter is being positioned, resulting in considerable loss of blood for the patient. The rate of backbleed is related to the outside diameter of the catheter so that as the catheter shaft diameter decreases, the rate of backbleed increases.

The object of the present invention is to seek to overcome the above difficulties.

The present invention provides a device for use with a catheter comprising a sleeve for assembly onto the shaft of a catheter, between the catheter shaft and a Tuohy-Borst connector, the internal diameter of the sleeve being complementary with the external diameter of the catheter so that the catheter is movable within the sleeve and the external diameter of the sleeve is such that when the Tuohy-Borst connector is closed, a seal is formed between the sleeve and the connector.

Preferably, the sleeve has a flange at one end thereof for engagement with the connector, to prevent movement of the sleeve with the catheter.

Advantageously, the internal diameter of the sleeve is complementary with the external diameter of the catheter so as to provide an annular space about the catheter whereby, in use, a controlled amount of backbleed of blood is allowed. The controlled backbleed prevents thrombosis which would otherwise occur when blood collects in restricted spaces.

Alternatively, a seal may be provided about the external surface of the sleeve so as to eliminate blood flow. Conveniently, the seal is provided at or towards the distal end of the sleeve. In this way, blood is prevented from entering the restricted space of the connector.

Conveniently, a portion of the sleeve adjacent the flange is of an enlarged diameter relative to the diameter of the remainder of the sleeve thereby providing a shoulder intermediate the flange and the other end of the sleeve.

In use, the Tuohy-Borst connector closes onto the external diameter of the sleeve, thus creating a seal between the Tuohy-Borst connector without impairing freedom of movement of the catheter within the sleeve. The effect of the device is to considerably reduce (though not totally eliminate) the backbleed of blood which occurs between the catheter and the internal diameter of the sleeve.

The device may be composed of any suitable material such as a metal or plastic, and may if required be coated with a non-stick material such as PTFE. The sleeve portion of the device must however be sufficiently rigid to prevent the sealing ring of the Tuohy-Borst connector from restricting the internal diameter of the sleeve. The inner surface should have low frictional characteristics to allow for ease of movement of the catheter within it.

The term "catheter" is to be read as embracing both a guide wire and a probe.

The invention will now be described more particularly with reference to the accompanying drawings which show by way of example only, one embodiment of a device according to the invention.

Figure 1:
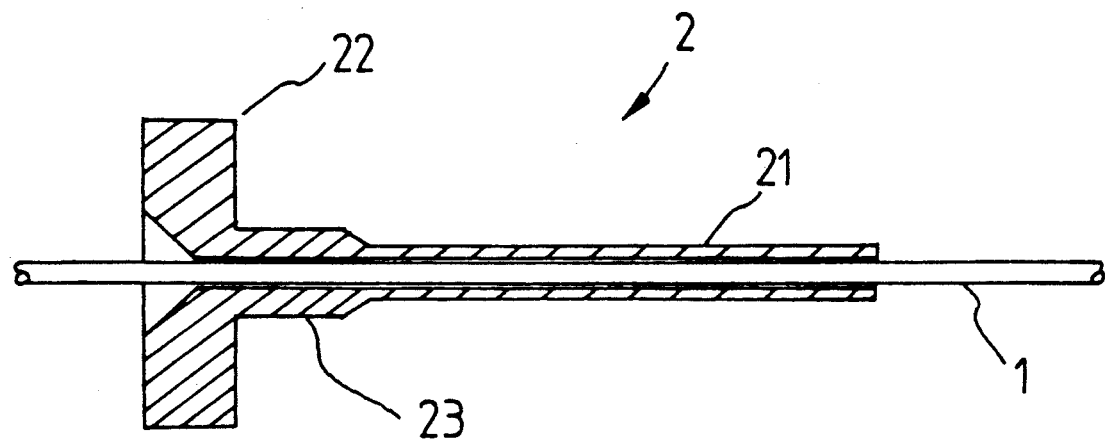
FIG. 1 is a cross-sectional side view of a device mounted on the shaft of a catheter.

Referring now to FIG. 1, the catheter 1 is engaged with a device 2 having a sleeve 21 with a flange 22. The internal diameter of the sleeve 21 is complementary with the external diameter of the catheter 1. The end of the sleeve 1 adjacent the flange 22 has a shoulder 23 which strengthens the device.

Figure 2:
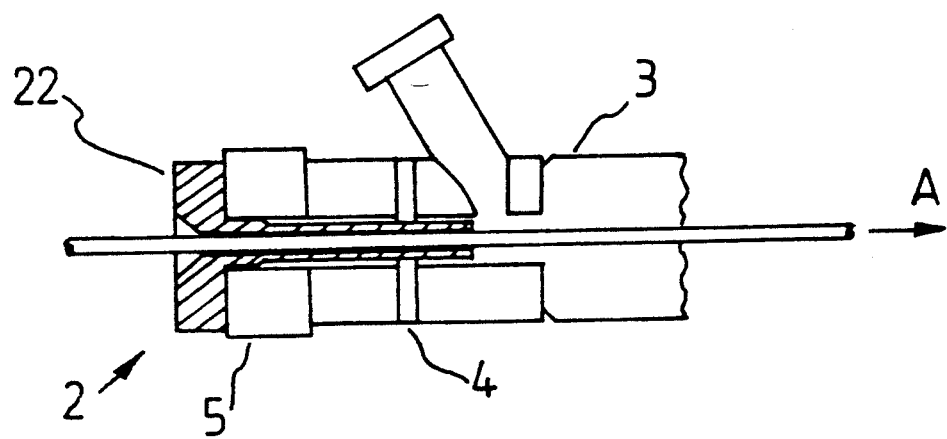
FIG. 2 is a sectional view as in FIG. 1 showing additionally a Tuohy-Borst connector engaged with the device.
Figure 3:
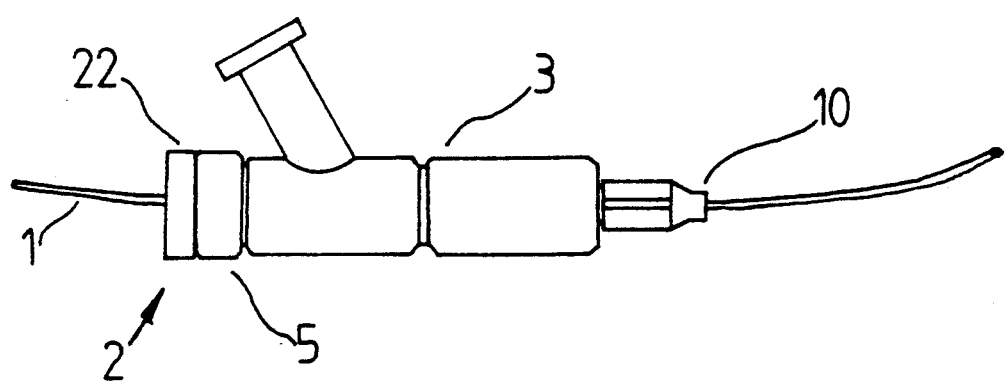
FIG. 3 is a side view of an assembly of a Tuohy-Borst connector sleeve, guide catheter and probe.

Turning now to FIGS. 2 and 3, the catheter 1 and device 2 have a Tuohy-Borst connector 3 mounted thereon. The connector 3 may be tightened or loosened on the assembly by engagement or release respectively of the sealing ring 4 by means of the screw 5. A guide catheter 10 is connected to the other end of the connector 3.

In use, the screw 5 is tightened to exert pressure on the sleeve 2 but not on the guide wire or catheter 1, thus stemming backbleed between the connecter 3 and sleeve 2 but not between the sleeve 2 and catheter 1. Such an arrangement allows the catheter 1 to be moved, but considerably reduces backbleed which would otherwise occur, in the absence of the sleeve 2. While the catheter 1 is being moved into the blood vessel, in the direction shown by the arrow A, the sleeve 2 is prevented from being displaced with the catheter 1 by virtue of the flange 22 which engages over the edges of the connector 3.

EXAMPLE 1

In the following example the leakage rate between an open Tuohy-Borst connector and a balloon catheter having a PTFE sleeve was determined.

The Tuohy-Borst was left in an open position thereby ensuring that the normal blood pressure (120/80) would be completely exerted on the Teflon sleeve. Using water, a pressure of 120 mm Hg was induced into the entire system and the leakage rate was measured over a period of 5 mins.

Sleeve ID 0.047", 3.5 F Shaft Diameter.

RESULTS

Quantity after 5 mins.=2.5 ml.
Leakage rate=0.5 ml/min.

With water leaking at this rate, it may be correct to suggest that with blood, which has a viscosity approximately 3.5 times greater than that of water, the leakage rate would be adversely affected i.e. leakage rate would be lower.

EXAMPLE 2

A similar procedure to that of example 1 was carried out using a solution of glycerine and milk, which possessed similar flow characteristics as blood. No significant difference from water was found in the leakage rate.

We claim:

1. A holding system for catheters of predetermined external diameters, said system including a connector with proximal and distal ends adapted to receive freely a catheter therethrough introduced through said proximal end, seal means within said connector for engaging a received catheter and providing a seal between said connector and the received catheter; the improvement comprising a sleeve received through said proximal end of said connector in surrounding relation to a received catheter and between the received catheter and said connector, said sleeve having an internal diameter greater than and complementary with the external diameter of the received catheter to define a space about the received catheter within and along the length of said sleeve sufficient to allow backbleed of blood therethrough in a controlled manner, said seal means engaging with said sleeve and providing a seal between said connector and said sleeve, said sleeve precluding engagement of said seal means with the received catheter and being of sufficient rigidity to maintain said defined space for a controlled amount of backbleed of blood therethrough.

2. A device as claimed in claim 1 in which said sleeve has an end with a flange thereon for engagement with said proximal end of said connector, to prevent movement of said sleeve with the catheter into said connector.

3. A device as claimed in claim 2 in which a portion of said sleeve adjacent the flange is of an enlarged diameter relative to the diameter of the remainder of said sleeve thereby providing a shoulder intermediate said flange and the other end of said sleeve.

4. A device as claimed in either claim 1 or claim 2 which is manufactured from a material having low frictional characteristics.

5. A device as claimed in claim 1, wherein said seal means comprises a sealing element provided about the exterior of said sleeve, said sealing element being adapted to co-operate with the interior of said connector to eliminate blood flow therebetween.

6. A device as claimed in claim 5, in which said sealing element is provided towards an end of said sleeve positionable inward of the proximal end of said connector.

* * * * *